United States Patent

Jorgensen et al.

Patent Number: 6,075,036
Date of Patent: *Jun. 13, 2000

[54] PYRROLO [2,1,5-CD] INDOLIZINE DERIVATIVES USEFUL IN THE PREVENTION OR TREATMENT OF ESTROGEN RELATED DISEASES OR SYNDROMES

[75] Inventors: Anker Steen Jorgensen, Copenhagen Y; Poul Jacobsen, Slangerup; Lise Brown Christiansen, Lyngby; Paul Stanley Bury, Copenhagen NV; Anders Kanstrup, Espergaerde, all of Denmark

[73] Assignees: Novo Nordisk, Bagsvaerd, Denmark; Karo Bio AB, Huddinge, Sweden

[*] Notice: This patent is subject to a terminal disclaimer.

[21] Appl. No.: 09/088,471

[22] Filed: Jun. 1, 1998

Related U.S. Application Data

[60] Provisional application No. 60/049,063, Jun. 10, 1997.

[30] Foreign Application Priority Data

Jun. 4, 1997 [DK] Denmark ................................ 0654/97

[51] Int. Cl.⁷ .......................... A61K 31/44; C07D 471/12
[52] U.S. Cl. ............................................. 514/294; 546/94
[58] Field of Search ................................ 546/94; 514/294

[56] References Cited

U.S. PATENT DOCUMENTS 2,986,563   5/1961   Boekelheide et al. ..................... 546/94

OTHER PUBLICATIONS

Tsuchiya et al. "thermal intramolecular cyclization of 2–ethynylpyridine N–ylides to indolizines and cyclazines" Chem. Phar. bull. v.32(11) 4666–4669, 1985.

Pohjala "Indolizine Derivatives IX . . . " J. Het. Chem. vol. 15(6) 955–960 1978.

*Primary Examiner*—Ceila Chang
*Attorney, Agent, or Firm*—Steve T. Zelson; Carol E. Rozek

[57] ABSTRACT

The present invention relates to therapeutically active compounds of formula I

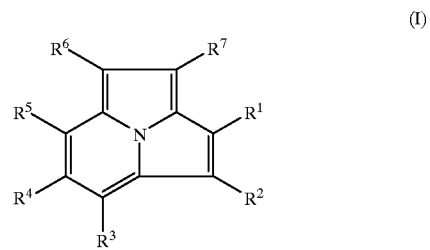

a method of preparing the same and to pharmaceutical compositions comprising the compounds. The novel compounds are useful in the prevention or treatment of estrogen related diseases or syndromes.

17 Claims, No Drawings

PYRROLO [2,1,5-CD] INDOLIZINE DERIVATIVES USEFUL IN THE PREVENTION OR TREATMENT OF ESTROGEN RELATED DISEASES OR SYNDROMES

CROSS-REFERENCE TO RELATED APPLICATIONS

This application claims priority of provisional application No. 60/049,063 filed Jun. 10, 1997, and of Danish application 0654/97 filed Jun. 4, 1997, the contents of which are fully incorporated herein by reference.

FIELD OF THE INVENTION

The present invention relates to new pyrrolo[2,1,5-cd] indolizine derivatives and the use of such compounds in the prevention or treatment of estrogen related diseases or syndromes, preferably diseases or syndromes caused by an estrogen-deficient state in a mammal, in particular bone loss, osteoporosis, cardiovascular diseases, cognitive disorders, senile dementia-Alzheimer's type, menopausal symptoms, including flushing and urogenital atrophy, dysmenorrhea, threatened or habitual abortion, dysfunctional uterine bleeding, acne, hirsutism, prostatic carcinoma, post-partum lactation, and the use of such compounds in a contraceptive method or as an aid in ovarian development.

BACKGROUND OF THE INVENTION

The osteopenia that accompanies the menopause continues to represent a major public health problem. Left unchecked, the cumulative loss of bone can potentially compromise the skeleton's structural integrity, resulting in painful and debilitating fractures of the wrist, spine and femur. Efforts to reduce the risk and incidence of fractures have focused on the development of therapies that conserve skeletal mass by inhibiting bone resorption. Among various treatment modalities, estrogen replacement therapy remains the preferred means to prevent the development of post menopausal osteoporosis (Lindsey R, Hart D M, MacClean A 1978, "The role of estrogen/progestogen in the management of the menopause", Cooke I D, ed, Proceedings of University of Sheffield symposium on the role of estrogen and progestogen in the management of the menopause, Lancaster, U K: MTP Press Ltd. pp. 9–25; Marshall D H, Horsmann A, Nordin B E C 1977, "The prevention and management of post-menopausal osteoporosis.", Acta Obstet Gynecol Scand (Suppl) 65:49–56; Recker R R, Saville P D, Heaney R P 1977, "Effect of estrogen and calcium carbonate on bone loss in post-menopausal women", Ann Intern Med. 87:649–655; Nachtigall L E, Nachtigall R H, Nachtigall R D, Beckman E M 1979, "Estrogen replacement therapy", Obstet Gynecol. 53:277–281) and it is now accepted that estrogens significantly decrease fracture incidence and risk (Krieger N, Kelsey J L, Holford T R, O'Connor T 1982, "An epidemiological study of hip fracture in postmenopausal women", Am J Epidemiol. 116:141–148; Hutchinson T A, Polansky S M, Feinstein A R 1979, "Post-menopausal estrogens protect against fractures of hip and distal radius: A case-control study", Lancet 2:705–709; Paginini-Hill A, Ross R K, Gerkins V R, Henderson B E, Arthur M, Mack T M 1981, "Menopausal oestrogen therapy and hip fractures", Ann Intern Med. 95:28–31; Weiss N S, Ure C L, Ballard J H, Williams A R, Daling J R 1980, "Decreased risk of fractures on the hip and lower forearm with post-menopausal use of estrogen", N Eng J Med. 303:1195–1198).

While the beneficial actions of estrogen replacement therapy on the skeleton are clearly significant, there is also considerable evidence for a positive effect of estrogen on the cardiovascular system. Previous studies have attributed these actions to estrogen's effects on serum lipids, but recent data has now shown that in addition to the effects on the lipid profile, estrogen can also directly influence vessel wall compliance, reduce peripheral resistance and prevent atherosclerosis (Lobo R A 1990, "Cardiovascular implication of estrogen replacement therapy", Obstetrics and Gynaecology, 75:18S–24S; Mendelson M E, Karas R H 1994, "Estrogen and the blood vessel wall", Current Opinion in Cardiology, 1994(9):619–626). Based on available epidemiological data, the overall impact of these physiological and pharmacological actions of estrogen is an age independent reduction in cardiovascular mortality and morbidity in women (Kannel W H, Hjortland M, McNamara P M 1976 "Menopause and risk of cardiovascular disease: The Framingham Study", Ann Int Med, 85:447–552). Furthermore, a more recent analysis has concluded that post-menopausal estrogen replacement therapy reduces the risk of cardiovascular disease by approximately 50 percent (Stampfer M J, Colditz G A 1991, "Estrogen replacement therapy and coronary heart disease: a quantitative assessment of the epidemiological evidence", Preventive Medicine, 20:47–63.).

In addition to the positive effects of estrogen on bone and cardiovascular system, there are now data which indicate that the central nervous system can benefit from estrogen replacement therapy. Short term studies in human subjects have shown that increased levels of estrogen are associated with higher memory scores in post menopausal women (Kampen D L, Sherwin B B 1994, "Estrogen use and verbal memory in healthy postmenopausal women", Obstetrics and Gynecology, 83(6):979–983). Furthermore, the administration of exogenous estrogen to surgically post menopausal women specifically enhances short-term memory. Moreover, the effects of estrogen on cognition do not appear confined to short-term effects as epidemiological findings indicate that estrogen treatment significantly decreases the risk of senile dementia-Alzheimer's type in women (Paganini-Hill A, Henderson V W, 1994, "Estrogen deficiency and risk of Alzheimer's disease in women", Am J Epidemiol, 140:256–261; Ohkura T, Isse K, Akazawa K, Hamamoto M, Yoshimasa Y, Hagino N, 1995, "Long-term estrogen replacement therapy in female patients with dementia of the Alzheimer Type: 7 case reports", Dementia, 6:99–107). While the mechanism whereby estrogens enhance cognitive function is unknown, it is possible to speculate that the direct effects of estrogen on cerebral blood flow (Goldman H, Skelley E b, Sandman C A, Kastin A J, Murphy S, 1976, "Hormones and regional brain blood flow", Pharmacol Biochem Rev. 5(suppl 1): 165–169; Ohkura T, Teshima Y, Isse K, Matsuda H, Inoue T, Sakai Y, Iwasaki N, Yaoi Y, 1995, "Estrogen increases cerebral and cerebellar blood flows in postmenopausal women", Menopause: J North Am Menopause Soc. 2(1):13–18) and neuronal cell activities (Singh M, Meyer E M, Simpkins J W, 1995, "The effect of ovariectomy and estradiol replacement on brain-derived neurotrophic factor messenger ribonucleic acid expression in cortical and hippocampal brain regions of female Sprague-Dawley rats", Endocrinology, 136:2320–2324; McMillan P J, Singer C A, Dorsa D M, 1996, "The effects of ovariectomy and estrogen replacement on trkA and choline acetyltransferase mRNA expression in the basal forebrain of the adult female Sprague-Dawley rat", J Neurosci., 16(5):1860–1865) are potential effectors for these beneficial actions.

The therapeutic applications of naturally occurring estrogens and synthetic compositions demonstrating estrogenic activity alone or in combination are not limited to the chronic conditions described above. Indeed, the more traditional applications of estrogen therapies would include the following: relief of menopausal symptoms (i.e. flushing and urogenital atrophy); oral contraception; prevention of threatened or habitual abortion, relief of dysmenorrhea; relief of dysfunctional uterine bleeding; an aid in ovarian development; treatment of acne; diminution of excessive growth of body hair in women (hirsutism); treatment of prostatic carcinoma: and suppression of post-partum lactation [Goodman and Gilman, The Pharmacological Basis of Therapeutics (Seventh Edition) Macmillan Publishing Company, 1985, pages 1421–1423].

Even though the beneficial effects of estrogen replacement on a wide variety of organ systems and tissues appear indisputable, the dose and duration of estrogen therapy is also associated with an increased risk of endometrial hyperplasia and carcinoma. The use of concomitant cyclic progestins does reduce the risk of endometrial pathology, but this is achieved at the expense of the return of regular menstruation, a result that is objectionable to many patients. In addition to estrogen's stimulatory effect on the endometrium, there remains considerable controversy regarding reports of an association between long-term estrogen replacement and an increased risk of breast cancer (Bergkvist L, Adami H O, Persson I, Hoover R, Schairer C, 1989, "The risk of breast cancer after estrogen and estrogen-progestin replacement", N Eng J Med, 321:293–297; Colditz G A, Hankinson S E, Hunter D J, Willett W C, Manson J E, Stampfer M J, Hennekens C, Rosner B, Speizer F E, 1995, "The use of estrogens and progestins and the risk of breast cancer in postmenopausal women", N Eng J Med, 332(24):1589–1593). Furthermore, there are other side effects of estrogen replacement which, while they may not be life threatening, contraindicate estrogen's use and reduce patient compliance. From the foregoing discussion it would appear that the availability of therapies which could mimic the beneficial actions of estrogen on the bone, cardiovascular system, and central nervous system without the undesirable side effects on uterus and breast, would essentially provide a "safe estrogen" which could dramatically influence the number of patients that would be able to benefit from estrogen replacement therapy. Therefore, in recognition of estrogen's beneficial effects on a number of body systems and disease conditions, there is a continuing need for the development of estrogen agonists which can selectively target different body tissues.

U.S. Pat. No. 2,986,563 discloses a class of cyclazines which has been disclaimed from the present application. However, there is no teaching or suggestion in this document that these compounds are active at the estrogen receptor.

DESCRIPTION OF THE INVENTION

The present invention provides compounds of formula I

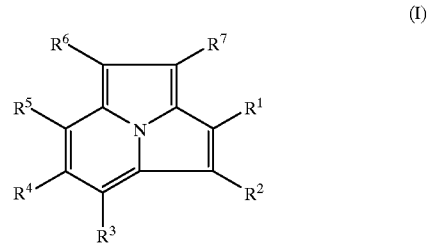

(I)

wherein $R^1$ is phenyl optionally substituted with one or two substituents selected from halogen, $CH_3$, OH, $OCH_3$, $OCOCH_3$ or benzyloxy; and $R^2$ is H, $C_{1-4}$-alkyl or $CO-R^8-O-R^9-NR^{10}R^{11}$, wherein $R^8$ is phenylene, $R^9$ is $C_{1-2}$-alkylene and $R^{10}$ and $R^{11}$ together with the nitrogen atom form a piperidino ring; and $R^3$ is H; and $R^4$ is H, OH, $OCH_3$ or $OCOCH_3$; and $R^5$ is H, OH or benzyloxy; and $R^6$ is H, halogen, $C_{1-2}$-alkyl, $COCH_3$, COOH, $COOCH_3$, $CO-R^{12}-NR^{13}R^{14}$, $R^{15}-NR^{13}R^{14}$ or phenyl optionally substituted with OH or benzyloxy, wherein $R^{12}$ is $C_{1-2}$-alkylene, $R^{15}$ is $C_{1-7}$-alkylene and $R^{13}$ and $R^{14}$ together with the nitrogen atom form a piperidino ring; and $R^7$ is H, halogen, $C_{1-2}$-alkyl, $COCH_3$, COOH, $COOCH_3$, $CO-NR^{16}R^{17}$, $O-R^{18}-O-R^{19}-NR^{20}R^{21}$, $CO-R^{18}-O-R^{19}-NR^{20}R^{21}$, $R^{18}-O-R^{19}-NR^{20}R^{21}$ or $R^{22}-NR^{20}R^{21}$, wherein $R^{16}$ and $R^{17}$ independently are H or $CH_3$, $R^{18}$ is phenylene, $R^{19}$ is $C_{1-2}$-alkylene, $R^{20}$ and $R^{21}$ together with the nitrogen atom form a piperidino ring and $R^{22}$ is $C_{1-7}$-alkylene, provided that neither $R^4$ nor $R^5$ is H when $R^1$ is unsubstituted phenyl;

or geometric or optical isomers, pharmaceutically acceptable esters, ethers or salts thereof.

The general chemical terms used in the above formula have their usual meanings.

The term $C_{1-7}$-alkyl includes straight-chained as well as branched alkyl groups such as methyl, ethyl, propyl, isopropyl, butyl, s-butyl, isobutyl, pentyl, neopentyl, hexyl, heptyl and the like.

The term $C_{1-7}$-alkylene includes straight or branched alkylene groups such as methylene, ethylene, trimethylene, tetramethylene, pentamethylene, hexamethylene, heptamethylene, propylene, ethylethylene and the like.

The term halogen means chloro, bromo, iodo and fluoro.

The compounds of this invention are new estrogen agonists and are useful for prevention and treatment of osteoporosis; the prevention and treatment of cardiovascular disease; treatment and prevention of physiological disorders associated with an excess of neuropeptide Y (e.g. obesity, depression, etc.); and for regulation of glucose metabolism in e.g. non-insulin dependent diabetes melitus; and the prevention and treatment of senile dementia-Alzheimer's type in women. In addition, these estrogen agonists are useful for oral contraception; relief of menopausal symptoms (e.g. hot flushes, urogenital atrophy, depression, mania, schizophrenia, etc.); incontinence; prevention of threatened or habitual abortion; relief of dysmenorrhea; relief of dysfunctional uterine bleeding; an aid in ovarian development; treatment of acne; diminution of excessive growth of body hair in women (hirsutism); treatment of prostatic carcinoma; and the suppression of post-partum lactation. These agents also lower serum cholesterol and have a beneficial effect on plasma lipid profiles.

While the compounds of this invention are estrogen agonists in bone and cardiovascular tissues, they are also capable of acting as antiestrogens in other estrogen target organs. For example, these compounds can act as antiestrogens in breast tissue and the colon and therefore would be useful for the prevention and treatment of estrogen-dependent cancers such as breast cancers and colon cancers.

The term "treatment" includes treatment, prevention and prophylaxis of the above mentioned diseases/indications/conditions or alleviation of the characteristic symptoms of such diseases/indications/conditions.

The preferred compounds of this invention are those in which:

$R^1$ is phenyl optionally substituted with OH or OCH$_3$;
$R^2$ is C$_{1-3}$-alkyl;
$R^4$ is H, OH or OCH$_3$;
$R^5$ is H or OH;
$R^6$ is CO—R$^{12}$—NR$^{13}$R$^{14}$ or R$^{15}$—NR$^{13}$ R$^{14}$ wherein R$^{12}$ is as defined above, R$^{15}$ is C$_{4-7}$-alkylene, and R$^{13}$ and R$^{14}$ are as defined above;
$R^7$ is R$^{18}$—O—R$^{19}$—NR$^{20}$R$^{21}$ and R$^{22}$—NR$^{19}$R$^{20}$ wherein R$^{18}$ and R$^{19}$ are defined above, R$^{22}$ is C$_{4-7}$-alkylene, and R$^{20}$ and R$^{21}$ are as defined above.

The most preferred compounds are the following:
Dimethyl 4-ethyl-6-methoxy-3-(4-methoxyphenyl)pyrrolo[2,1,5-cd]indolizine-1,2-dicarboxylate,
4-Ethyl-6-methoxy-3-(4-methoxyphenyl)pyrrolo[2,1,5-cd]indolizine-1,2-dicarboxylic acid,
1-Ethyl-6-methoxy-2-(4-methoxyphenyl)pyrrolo[2,1,5-cd]indolizine,
1-Ethyl-6-hydroxy-2-(4-hydroxyphenyl)pyrrolo[2,1,5-cd]indolizine,
6-Acetoxy-2-(4-acetoxyphenyl)-1-ethylpyrrolo[2,1,5-cd]indolizine,
4-Acetyl-1-ethyl-6-methoxy-2-(4-methoxyphenyl)pyrrolo[2,1,5-cd]indolizine,
4-Acetyl-1-ethyl-2-(4-hydroxyphenyl)-6-methoxypyrrolo[2,1,5-cd]indolizine,
4-Acetyl-1-ethyl-6-hydroxy-2-(4-hydroxyphenyl)pyrrolo[2,1,5-cd]indolizine,
Methyl 6-methoxy-3-(4-methoxyphenyl)-4-methylpyrrolo[2,1,5-cd]indolizine-1-carboxylate,
Dimethyl 4-ethyl-3-(4-fluorophenyl)-6-methoxypyrrolo[2,1,5-cd]indolizine-1,2-dicarboxylate,
Dimethyl 6-methoxy-3-(4-methoxyphenyl)-4-methylpyrrolo[2,1,5-cd]indolizine-1,2-dicarboxylate,
Dimethyl 6-methoxy-4-methyl-3-phenylpyrrolo[2,1,5-cd]indolizine-1,2-dicarboxylate,
Dimethyl 4-ethyl-3-(4-methoxyphenyl)pyrrolo[2,1,5-cd]indolizine-1,2-dicarboxylate,
Dimethyl 4-ethyl-6-methoxy-3-phenylpyrrolo[2,1,5-cd]indolizine-1,2-dicarboxylate,
Dimethyl 3-(4-benzyloxyphenyl)pyrrolo[2,1,5-cd]indolizine-1,2-dicarboxylate,
Dimethyl 7-benzyloxy-3-(4-benzyloxyphenyl)pyrrolo[2,1,5-cd]indolizine-1,2-dicarboxylate,
Dimethyl 6-methoxy-3-(4-methoxyphenyl)pyrrolo[2,1,5-cd]indolizine-1,2-dicarboxylate,
Dimethyl 4-ethyl-3-(3-methoxyphenyl)pyrrolo[2,1,5-cd]indolizine-1,2-dicarboxylate,
Dimethyl 4-ethyl-3-(3-fluoro-4-methoxyphenyl)pyrrolo[2,1,5-cd]indolizine-1,2-dicarboxylate,
Dimethyl 4-n-butyl-3-(4-methoxyphenyl)pyrrolo[2,1,5-cd]indolizine-1,2-dicarboxylate,
Dimethyl 4-ethyl-3-(4-methoxy-2-methylphenyl)pyrrolo[2,1,5-cd]indolizine-1,2-dicarboxylate,
4-Ethyl-3-(4-fluorophenyl)-6-methoxypyrrolo[2,1,5-cd]indolizine-1,2-dicarboxylic acid,
6-Methoxy-3-(4-methoxyphenyl)-4-methylpyrrolo[2,1,5-cd]indolizine-1,2-dicarboxylic acid,
4-Ethyl-3-(4-n-ethoxyphenyl)pyrrolo[2,1,5-cd]indolizine-1,2-dicarboxylic acid,
4-Ethyl-6-methoxy-3-phenylpyrrolo[2,1,5-cd]indolizine-1,2-dicarboxylic acid,
3-(4-Benzyloxyphenyl)pyrrolo[2,1,5-cd]indolizine-1,2-dicarboxylic acid,
7-Benzyloxy-3-(4-benzyloxyphenyl)pyrrolo[2,1,5-cd]indolizine-1,2-dicarboxylic acid,
6-Methoxy-3-(4-methoxyphenyl)pyrrolo[2,1,5-cd]indolizine-1,2-dicarboxylic acid,
4-Ethyl-3-(3-methoxyphenyl)pyrrolo[2,1,5-cd]indolizine-1,2-dicarboxylic acid,
4-Ethyl-3-(3-fluoro-4-methoxyphenyl)pyrrolo[2,1,5-cd]indolizine-1,2-dicarboxylic acid,
4-n-Butyl-3-(4-methoxyphenyl)pyrrolo[2,1,5-cd]indolizine-1,2-dicarboxylic acid,
4-Ethyl-3-(4-methoxy-2-methylphenyl)pyrrolo[2,1,5-cd]indolizine-1,2-dicarboxylic acid,
1-Ethyl-2-(4-fluorophenyl)-6-methoxypyrrolo[2,1,5-cd]indolizine,
1-Ethyl-2-(4-methoxyphenyl)pyrrolo[2,1,5-cd]indolizine,
1-Ethyl-6-methoxy-2-phenylpyrrolo[2,1,5-cd]indolizine,
1-Ethyl-2-(3-methoxyphenyl)pyrrolo[2,1,5-cd]indolizine,
5-Benzyloxy-2-(4-benzyloxyphenyl)pyrrolo[2,1,5-cd]indolizine,
6-Methoxy-2-(4-methoxyphenyl)pyrrolo[2,1,5-cd]indolizine,
2-(4-Benzyloxyphenyl)pyrrolo[2,1,5-cd]indolizine,
1-Ethyl-2-(3-fluoro-4-methoxyphenyl)pyrrolo[2,1,5-cd]indolizine,
1-n-Butyl-2-(4-methoxyphenyl)pyrrolo[2,1,5-cd]indolizine,
1-Ethyl-2-(4-methoxy-2-methylphenyl)pyrrolo[2,1,5-cd]indolizine,
4-Acetyl-1-ethyl-2-(4-methoxyphenyl)pyrrolo[2,1,5-cd]indolizine,
6-Hydroxy-2-(4-methoxyphenyl)pyrrolo[2,1,5-cd]indolizine,
6-Hydroxy-2-(4-hydroxyphenyl)pyrrolo[2,1,5-cd]indolizine,
1-Ethyl-6-hydroxy-2-phenylpyrrolo[2,1,5-cd]indolizine,
1-Ethyl-2-(3-hydroxyphenyl)pyrrolo[2,1,5-cd]indolizine,
4-Acetyl-1-ethyl-2-(4-hydroxyphenyl)pyrrolo[2,1,5-cd]indolizine,
1-Ethyl-2-(3-fluoro-4-hydroxyphenyl)pyrrolo[2,1,5-cd]indolizine,
1-Ethyl-2-(4-hydroxy-2-methylphenyl)pyrrolo[2,1,5-cd]indolizine,
1-n-Butyl-2-(4-hydroxyphenyl)pyrrolo[2,1,5-cd]indolizine,
1-Ethyl-2-(4-hydroxyphenyl)pyrrolo[2,1,5-cd]indolizine,
5-Hydroxy-2-(4-hydroxyphenyl)pyrrolo[2,1,5-cd]indolizine,
2-(4-Hydroxyphenyl)pyrrolo[2,1,5-cd]indolizine,
1-Ethyl-6-hydroxy-2-(4-hydroxyphenyl)-3-[4-(2-piperidinoethoxy)benzoyl]pyrrolo[2,1,5-cd]indolizine,
1-Ethyl-2-(4-hydroxyphenyl)-3-(6-piperidinohexyl)pyrrolo[2,1,5-cd]indolizine,
1-Ethyl-2-(4-hydroxyphenyl) -3-[4-(2-piperidinoethoxy)benzoyl]pyrrolo[2,1,5-cd]indolizine, 1-Ethyl-2-(3-fluoro-4-hydroxyphenyl)-3-[4-(2-piperidinoethoxy)phenyl]pyrrolo[2,1,5-cd]indolizine,
1-Ethyl-2-(4-hydroxyphenyl)-4-(1-oxo-3-piperidino propyl)pyrrolo[2,1,5-cd]indolizine,
1,4-Diethyl-2-(4-hydroxyphenyl)pyrrolo[2,1,5-cd]indolizine,
1-Ethyl-2-(4-methoxyphenyl)-4-(3-piperidinopropyl)pyrrolo[2,1,5-cd]indolizine,
1-Ethyl-2-(4-hydroxyphenyl)-4-(3-piperidinopropyl)pyrrolo[2,1,5-cd]indolizine,
1-Ethyl-2-(4-methoxyphenyl)-4-phenylpyrrolo[2,1,5-cd]indolizine,
1-Ethyl-2-(4-hydroxphenyl)-4-phenylpyrrolo[2,1,5-cd]indolizine,
1-Ethyl-4-(4-hydroxyphenyl)-2-(4-methoxyphenyl)pyrrolo[2,1,5-cd]indolizine,
1-Ethyl-2,4-bis-(4-hydroxyphenyl)pyrrolo[2,1,5-cd]indolizine,
1-Ethyl-2-(4-hydroxyphenyl)-3-methylpyrrolo[2,1,5-cd]indolizine,
4-Ethyl-3-(4-hydroxyphenyl)pyrrolo[2,1,5-cd]indolizine-2-carboxylic acid dimethylamide,
2-(4-Methoxyphenyl)-3-(4-(2-piperidinoethoxy)phenyl)pyrrolo[2,1,5-cd]indolizine,
2-(4-Hydroxyphenyl)-3-(4-(2-piperidinoethoxy)phenyl)pyrrolo[2,1,5-cd]indolizine,
1-Ethyl-2-(4-hydroxyphenyl)-3-(4-(2-piperidinoethoxy)phenyl)pyrrolo[2,1,5-cd]indolizine,
1-Ethyl-2-(4-methoxyphenyl)-3-(4-(2-piperidinoethoxy)phenyl)pyrrolo[2,1,5-cd]indolizine;

or geometric or optical isomers, pharmaceutically acceptable esters, ethers or salts thereof.

The preparation of cycl[3,2,2]azines (i.e. pyrrolo[2,1,5-cd]indolizines) is well described in Advances in heterocyclic chemistry Vol. 22, p. 321–365, 1978, Title: Cyclazines and related N-bridged Annulenes, and a general review is given in Synthesis, Vol. 4, p. 209–36, 1976, Title: Methods for the Construction of the Indolizine Nucleus". Preparation of the intermediate indolizines is also well described in the literature, i.a. in Russian Chemical Reviews, 44 (9), 1975; Title: Indolizines.

The invention is furthermore concerned with a general method for the preparation of compounds of formula (I) comprising the steps of:

a) reacting a compound of the formula (II)

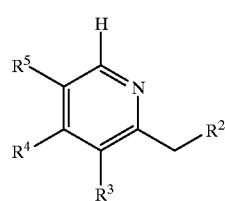

(II)

wherein $R^2$–$R^5$ are as defined above with a compound of the formula (III)

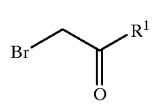

(III)

wherein $R^1$ is as defined above, in a suitable solvent, preferably acetone, acetonitrile or tetrahydrofuran, to form a compound of the formula (IV)

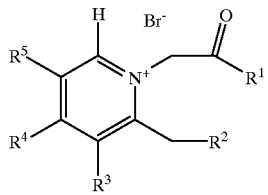

(IV)

wherein $R^1$–$R^5$ are as defined above;

b) reacting a compound of the formula (IV) with aqueous sodium hydrogen carbonate solution to form a compound of the formula (V)

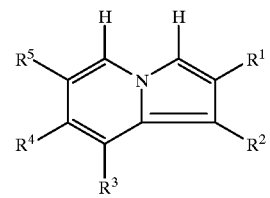

(V)

wherein $R^1$–$R^5$ are as defined above;

c) reacting a compound of the formula (V) with a compound of the formula (VI)

(VI)

wherein $R^6$ and $R^7$ independently are H, $COOCH_3$ or $COCH_3$, provided that at least one of $R^6$ and $R^7$ is $COOCH_3$ or $COCH_3$, in a suitable solvent, preferably toluene, and oxidizing the dihydro intermediate with 2,3-dichloro-5,6-dicyano-1,4-benzoquinone (DDQ) to form a compound of the formula (I) wherein $R^1$–$R^7$ are as defined above;

d) hydrolyzing a compound of formula (I) wherein $R^6$ and $R^7$ are independently COOCH3, with a suitable base, preferably potassium hydroxide in methanol, to give a compound of formula (I), wherein $R^6$ and $R^7$ are independently COOH and $R^1$–$R^5$ are as defined above;

e) decarboxylating a compound of formula (I), wherein $R^6$ and $R^7$ are independently COOH, preferably by reaction with copper in quinoline, to give a compound of formula (I), wherein $R^6$ and $R^7$ are H and $R^1$–$R^5$ are as defined above;

f) demethylating a compound of formula (I) wherein $R^1$ is methoxyphenyl optionally substituted with halogen or $CH_3$, and $R^4$ is H or $OCH_3$, with boron tribromide in methylene chloride or with pyridinium chloride fusion, to give a compound of formula (I), wherein $R^1$ is hydroxyphenyl optionally substituted with halogen or $CH_3$, and $R^4$ is H or OH and $R^2$, $R^3$, $R^5$, $R^6$ and $R^7$ are as defined above.

The invention furthermore relates to a method of synthesizing compounds of formula (I), which method comprises the steps of:

a) reacting a compound of formula (VII)

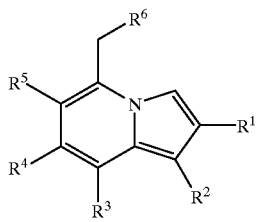

(VII)

wherein $R^1$–$R^6$ are as defined above, with n-butyllithium followed by the N,N-dimethylamide (VIII)

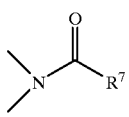

(VIII)

wherein $R^7$ is as defined above, followed by hydrolysis to form a compound (IX)

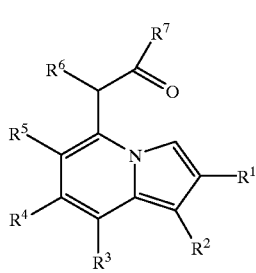

(IX)

wherein $R^1$–$R^7$ are as defined above; and b) ring closing the compound (IX) by treatment with acetic acid to form a compound of formula (I), wherein $R^1$–$R^7$ are as defined above;

The invention furthermore relates to a method of synthesizing compounds of formula (I), which comprises the steps of:

a) reacting a compound of formula (I), wherein $R^6$ and $R^7$ are hydrogen, with bromine in acetic acid to give a compound of formula (I), wherein $R^1$–$R^5$ are as defined above, $R^6$ is bromine and $R^7$ is hydrogen, b) reacting a compound of formula (I), wherein $R^6$ is bromine, with a phenylboronic acid under suitable Suzuki cross coupling conditions in the presence of a palladium(O) catalyst, preferably tetrakistriphenylphosphine palladium (O), to give a compound of formula (I), wherein $R^6$ is a phenyl or substituted-phenyl group, $R^1$–$R^5$ are as defined above and $R^7$ is hydrogen, c) debenzylating a compound of formula (I) wherein $R^1$ is benzyloxyphenyl and $R^5$ is either benzyloxy or H, using a palladium on carbon catalyst and hydrogen gas, to give a compound of formula (I), wherein $R^1$ is hydroxyphenyl and $R^5$ is H or OH and $R^2$, $R^3$, $R^4$, $R^6$ and $R^7$ are as defined above.

Examples of pharmaceutically acceptable salts include inorganic and organic acid addition salts such as hydrochloride, hydrobromide, sulphate, phosphate, acetate, fumarate, maleate, citrate, lactate, tartrate, oxalate, or similar pharmaceutically acceptable inorganic or organic acid addition salts, and include the pharmaceutically acceptable salts listed in *Journal of Pharmaceutical Science*, 66, 2 (1977) which are known to the skilled artisan. The compounds of this invention may form solvates with standard low molecular weight solvents using methods known to the skilled artisan.

In vitro estrogen receptor binding assay

An in vitro receptor binding assay was used to determine the estrogen receptor binding affinity of the compounds of this invention. This assay measures the ability of the compounds of this invention to displace $^3$H-17β-estradiol (17β-E2), from estrogen receptor (ER) obtained from rabbit uterus. Experimentally, the ER rich cytosol from rabbit uterine tissue is diluted with ER poor cytosol isolated from rabbit muscle to achieve approximately 20–25% maximal binding of 0.5 nM $^3$H-17β-3-E2. For each assay, fresh aliquots of cytosol are thawed on the day of analysis and diluted with assay buffer to ca. 3 mg cytosol protein/ml. The assay buffer (PB) is as follows: 10 mM $K_2HPO_4$/$KH_2PO_4$, 1.5 mM $K_2$EDTA, 10 mM monothioglycerol, 10 mM $Na_2MoO_4$.$2H_2O$, 10% glycerol (v/v); pH 7.5. Radio-inert 17β-3-E2 is obtained from Sigma. Test solutions are prepared in appropriate solvents (ethanol or DMSO) at a concentration of 8×10−3M and serial dilutions prepared with PB or DMSO. Aliquots of 10 μl are incubated in duplicate for each concentration tested in microtitre plates to which have been added 20 μl $^3$H-17β-E2 (assay concentration equals 0.4 nM) and 50 μl cytosol. For control samples as well as maximal binding sample, 10 μl PB is added in lieu of test compound.

Following an 18–20 hr incubation at 4° C. the reaction is terminated with 100 μl DCC slurry [0.5% activated charcoal (Sigma) and 0.005% Dextran T70 (Pharmacia) in PB] added to each sample and incubated with continuous shaking for 15 min at 4° C. DCC background counts are assessed using 50 μl of 0.3% BSA in PB in lieu of cytosol.

To separate bound and free $^3$H-17β-E2, Titertek plates are centrifuged for 10 min (800×g) at 4° C. and aliquots of 100 μl are removed from each sample for scintillaton counting using Opti-flour scintillation liquid. Standard and control samples are incubated in quadruplicate, while test compounds are incubated in duplicate. The mean counts per minute (cpm) in each sample is calculated, background (DCC) is subtracted, and the percent of maximal 3H-17β-E2 binding is determined. Individual cpm's are plotted against their respective concentrations of test compound (logarithmic scale), and the IC50 expressed as the compound concentration required to displace 50% of the maximal binding.

Bone Mineral Density

Bone mineral density (BMD) as a measure of bone mineral content (BMC) accounts for greater than 80% of a bone's strength. The loss of BMD with ageing and the accelerated loss following the menopause reduce the strength of the skeleton and render specific sites more susceptible to fracture; i.e. most notably the spine, wrist and hip. True bone density can be measured gravimetrically using Archimede's Principle (an invasive technique). The BMD can also be measured non-invasively using dual energy x-ray absorptiometry (DEXA). In our laboratory, we have utilized a gravimetric method to evaluate changes in BMD due to estrogen deficiency in ovariectomized rodents. Following ovariectomy (the surgical removal of the ovaries), the animals are treated with vehicle, 17β-E2 as a positive control, and/or other estrogen agonists. The objective of these investigations is to evaluate the ability of the compounds of this invention to prevent bone loss in rodent models of human disease.

Female Sprague-Dawley rats (ca. 3 to 5 months old), or female Swiss-Webster mice (ca. 3 to 5 months old) underwent bilateral ovariectomy or sham surgery. Following recovery from anesthesia the animals are randomized to the following groups, minimum of 8 animals per group:

sham animals treated with vehicle;
ovariectomized animals treated with vehicle;
ovariectomized animals treated with 25 µg estradiol/kg; and
ovariectomized animals treated with 200 µg/kg of test compound.

All compounds are weighed and dissolved in vehicle solvent in sterile saline and the animals are treated daily via subcutaneous injections for 35 days. At the conclusion of the 35 day protocol, the animals are sacrificed and the femora are excised and cleaned of adherent soft tissue. In rats, the distal 1 cm of the defleshed femora are removed with a diamond wheel cut-off saw and fixed in 70% ethyl alcohol (in mice the distal 0.5 cm are removed and fixed). Following fixation in 70% ethyl alcohol (EtOH) an automated tissue processor was used to dehydrate the bone specimens in an ascending series of alcohol to 100%. The dehydration program was followed by defatting in chloroform and rehydration in distilled water. All automated tissue processing occurred under vacuum. The hydrated bones were weighed in air and weighed while suspended in water on a Mettler balance equipped with a density measurement kit. The weight of each sample in air is divided by the difference between the air weight and the weight in water to determine total bone density; i.e. organic matrix plus mineral per unit volume of tissue. After the determination of total bone density the samples are ashed overnight in a muffle furnace at 600° C. The mineral density can then be determined by dividing the ash weight of each sample by the tissue volume (i.e. air weight-weight suspended in water). The mean bone densities (total and mineral bone densities) are calculated for each group and statistical differences from the vehicle-treated and estrogen-treated controls are determined using computerized statistical programs.

Cholesterol lowering activity

The effects of the compounds of the present invention on the serum levels of total cholesterol were measured either in blood samples taken from the animals in the bone density studies described above or from ovariectomized female rats or mice that had been treated with compound for a period of not less than 28 days. In each type of experiment, blood from treated animals was collected via cardiac puncture and placed in a tube containing 30 µl of 5% EDTA/1 ml of blood. Following centrifugation at 2500 rpm for 10 minutes at 20° C. the plasma was removed and stored at −20° C. until assayed. Cholesterol was measured using a standard enzymatic determination kit purchased from Sigma Diagnostics (Kit No. 352).

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen useful in the prevention or treatment of estrogen related diseases or syndromes it may frequently be necessary to begin with a dosage of from about 20 to about 70 mg per day and when the condition is under control to reduce the dosage as low as from about 0.1 to about 10 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, depot, subcutaneous, intravenous, intraurethral, intramuscular, intranasal, ophthalmic solution or an ointment, the oral route being preferred.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 0.1 to about 100 mg in a pharmaceutically acceptable carrier per unit dosage.

A typical tablet, appropriate for use in this method, may be prepared by conventional tabletting techniques and contains:

| Active compound | 5.0 mg |
|---|---|
| Lactosum | 67.8 mg Ph. Eur. |
| Avicel ® | 31.4 mg |
| Amberlite ® | 1.0 mg |
| Magnesii stearas | 0.25 mg Ph. Eur. |

The compounds according to this invention may be suitable for administration to an animal. Such animals include both domestic animals, for example livestock, laboratory animals, and household pets, and non-domestic animals such as wildlife. More preferably, the animal is a vertebrate. Most preferably, a compound according to this invention shall be administered to a mammal. It is especially preferred that the animal is a domestic mammal or a human. The most preferred mammal is a human. For such purposes, a compound of this invention may be administered as a feed additive or in bulk form.

The invention is explained more in detail in the below examples, which illustrate the invention. It is not to be considered as limiting the scope of the invention being defined by the appended claims.

EXAMPLE 1

Dimethyl 4-ethyl-6-methoxy-3-(4-methoxyphenyl) pyrrolo[2,1,5-cd]indolizine-1,2-dicarboxylate Step 1:
2-n-Propylpyridine-N-oxide To a solution of 2-n-propylpyridine (187.4 g, 1.505 mol) in 900 ml of acetic acid was added 149 ml of 35% aqueous hydrogen peroxide and the mixture was stirred and heated to 70–80° C. After three hours a further 104 ml of the hydrogen peroxide solution was added, and the mixture was maintained at the same temperature for an additional nine hours. The mixture was concentrated to about 300 ml in volume, 300 ml of water were added, and the mixture again concentrated as far as possible. The residue was made alkaline with anhydrous sodium carbonate, shaken with 750 ml of dichloromethane, and allowed to stand overnight. The resulting deposit of sodium carbonate and sodium acetate was removed by filtration. The filtrate was dried with magnesium sulfate, the solvent removed, and the residue distilled in vacuo. The yield of 2-n-propylpyridine-N-oxide, b.p. 120–140° C./9–15 mbar, was 176 g (81%). $^1$H-NMR (CDCl$_3$, 200 MHz) δ: 1.05 (t, 3H), 1.80 (sext, 2H), 2.89 (t, 2H), 7.10–7.28 (m, 3H), 8.28 (d, 1H).

Step 2:
4-Nitro-2-n-propylpyridine-N-oxide

A mixture of 2-n-propylpyridine-N-oxide (137.2 g, 1.0 mol) in 200 ml of sulfuric acid (sp.gr. 1.84) was stirred in an ice-salt bath and 320 ml of nitric acid (sp.gr. 1.52) was added. The mixture was carefully heated to 70–72° C. and reacted for 22 hours. The reaction mixture was cooled and poured onto ice and, with stirring, neutralized with portions of sodium carbonate (500 g). The resulting precipitate was collected, washed with water and dried. The dried substance was slurried in 1 liter of dichloromethane and anhydrous sodium sulfate was added. The mixture was filtered and the solvent was evaporated. The yellow residue from evaporation of the dichloromethane solution was dried to afford 89.2 g (49%) of 4-nitro-2-n-propylpyridine-N-oxide. M.p. 89–91° C. $^1$H-NMR (CDCl$_3$, 200 MHz) δ: 1.10 (t, 3H), 1.70 (sext, 2H), 2.94 (t, 2H), 7.96 (dd, 1H), 8.08 (dd, 1H), 8.30 (dd, 1H).

Step 3:
4-Methoxy-2-n-propylpyridine-N-oxide

A solution of 4-nitro-2-n-propylpyridine-N-oxide (146.0 g, 0.8 mol) in 500 ml of anhydrous methanol was stirred and 190 ml of a 4.6 M methanolic sodium methoxide solution was added dropwise. When the addition was complete, the mixture was stirred for three hours. The precipitated sodium nitrite was filtered off and washed with methanol. The filtrate was evaporated and the residue was stirred with 300 ml of dichloromethane. The mixture was filtered and evaporated to afford 129 g (97%) of 4-methoxy-2-n-propylpyridine-N-oxide as an oil. $^1$H-NMR (CDCl$_3$, 200 MHz) δ: 1.07 (t, 3H), 1.80 (sext, 2H), 2.80 (t, 2H), 3.87 (s, 3H), 6.66–6.78 (m, 2H), 8.17 (d, 2H).

Step 4:
4-Methoxy-2-n-propylpyridine

A solution of 4-methoxy-2-n-propylpyridine-N-oxide (59.3 g, 0.355 mol) in 800 ml of 1 M sulfuric acid was stirred and heated to 70–80° C. Zinc dust (140.0 g, 214 mol) was added in portions over four hours. When the addition was complete, heating was continued for a further eight hours. The resulting precipitate was filtered off and washed with water. The filtrate was made strongly alkaline by addition of a 32% sodium hydroxide solution and extracted with dichloromethane (3×250 ml). The extracts were combined, dried with sodium sulfate, filtered and evaporated to a yellow oil. Distillation (0.1–0.2 mbar, 44–46° C.) afforded 46.1 g (86%) of 4-methoxy-2-n-propylpyridine as a colourless oil. $^1$H-NMR (CDCl$_3$, 200 MHz) δ: 0.99 (t, 3H), 1.75 (sext, 2H), 2.72 (t, 2H), 3.81 (s, 3H), 6.10–6.18 (m, 2H), 8.35 (d, 1H).

Step 5:
1-Ethyl-7-methoxy-2-(4-methoxyphenyl) indolizine

A solution of 4-methoxy-2-n-propylpyridine (45.7 g, 0.3 mol) and 4-methoxyphenacylbromide (69.2 g, 0.3 mol) in 400 ml of dry acetone was heated to reflux for eight hours. The mixture was cooled and the precipitate was isolated and dried to afford 103.8 g (90%) of 4-methoxy-1-(4-methoxyphenacyl)-2-n-propylpyridinium bromide. The quaternary salt (103.8 g) was suspended in 480 ml of water and sodium hydrogen carbonate (102.0 g) was added. The mixture was refluxed for two hours. The resulting precipitate was filtered off, washed with water and dried to yield overall 73.2 g (86%) of 1-ethyl-7-methoxy-2-(4-methoxyphenyl) indolizine. M.p. 101–3° C. $^1$H-NMR (DMSO-d$_6$, 200 MHz) δ: 1.10 (t, 3H), 2.77 (q, 2H), 3.77 (s, 3H), 3.80 (s, 3H), 6.23 (dd, 1H), 6.65 (d, 1H), 7.00 (d, 2H), 7.35 (s, 1H), 7.38 (d, 2H), 8.06 (d, 1H).

Analysis: Calculated for $C_{18}H_{19}N_1O_2$. C, 76.84; H, 6.81; N, 4.98%. Found: C, 76.73; H, 6.94; N, 4.80%.

Step 6:
Dimethyl 4-ethyl-6-methoxy-3-(4-methoxyphenyl)pyrrolo [2,1,5-cd]indolizine-1,2-dicarboxylate A solution of 1-ethyl-7-methoxy-2-(4-methoxyphenyl) indolizine (25.0 g, 0.089 mol) in 800 ml of toluene was stirred in an ice bath, while dimethyl acetylenedicarboxylate (12.6 ml, 0.103 mol) was added dropwise. When the starting material had been consumed according to TLC, 2,3-dichloro-5,6-dicyano-1,4-benzoquinone (21.18 g, 0.093 mol) was added in portions. When the addition was complete, the mixture was refluxed for one hour. The resulting hydroquinone was filtered off, and the filtrate was concentrated to dryness. The residue was triturated with petroleum ether (40–60) and isolated to afford 33.8 g (92%) of the title compound. M.p. 153–5° C. $^1$H-NMR (DMSO-d$_6$, 200 MHz) δ: 1.36 (t, 3H), 3.07 (q, 2H), 3.76 (s, 3H), 3.86 (s, 3H), 3.89 (s, 3H), 4.10 (s, 3H), 7.15 (d, 2H), 7.53 (d, 2H), 7.84 (d, 1H), 8.00 (d, 1H). (Compound 1).

Analysis: Calculated for $C_{24}H_{23}N_1O_6$. C, 68.40; H, 5.50; N, 3.32%. Found: C, 68.48; H, 5.64; N, 3.27%.

EXAMPLE 2

4-Ethyl-6-methoxy-3-(4-methoxyphenyl)pyrrolo[2,1, 5-cd]indolizine-1,2-dicarboxylic acid A mixture of dimethyl 4-ethyl-6-methoxy-3-(4-methoxyphenyl)pyrrolo[2,1,5-cd]indolizine-1,2-dicarboxylate (2.3 g, 5.5 mmol) and 85% potassium hydroxide (11.5 g, 175 mmol) in 110 ml of methanol was refluxed for ten hours. The mixture was cooled and the yellow potassium salt isolated by filtration. The salt was dissolved in 125 ml of water and the pH was adjusted to 2.0 with a 6M hydrochloric acid solution. The precipitate was filtered off and dried to afford 2.08 g (95%) of the title compound. M.p. 209–11° C. $^1$H-NMR (DMSO-$d_6$, 200 MHz) δ: 1.34 (t, 3H), 3.00 (q, 2H), 3.85 (s, 3H), 4.08 (s, 3H), 7.10 (d, 2H), 7.55 (d, 2H), 7.85 (d, 1H), 7.94 (d, 1H). (Compound 2).

Analysis: Calculated for $C_{22}H_{19}N_1O_6$, 0.5 $H_2O$. C, 65.67; H, 5.01; N, 3.48%. Found: C, 65.80; H, 5.16; N, 3.20%.

EXAMPLE 3

1-Ethyl-6-methoxy-2-(4-methoxyphenyl)pyrrolo[2,1,5-cd]indolizine

A mixture of 4-ethyl-6-methoxy-3-(4-methoxyphenyl)pyrrolo[2,1,5-cd]indolizine-1,2-dicarboxylic acid (1.75 g, 4.45 mmol), copper powder (0.4 g), and 90 ml of freshly purified quinoline was heated to 170° C. for eight hours in a nitrogen atmosphere. The copper catalyst was filtered off and the filtrate acidified with 6M hydrochloric acid and extracted with ether. The washed and dried (magnesium sulfate) extract was evaporated and the residue triturated with petroleum ether (40–60). The precipitate was filtered off and dried to afford 1.05 g (77%) of the title compound. M.p. 109–11° C. $^1$H-NMR (DMSO-$d_6$, 200 MHz) δ: 1.38 (t, 3H), 3.18 (q, 2H), 3.85 (s, 3H), 4.02 (s, 3H), 7.12 (d, 1H), 7.14 (d, 2H), 7.60 (d, 1H), 7.70–7.80 (m, 4H). (Compound 3).

Analysis: Calculated for $C_{20}H_{19}N_1O_2$. C, 78.66; H, 6.27; N, 4.59%. Found: C, 79.05; H, 6.40; N, 4.46%.

EXAMPLE 4

1-Ethyl-6-hydroxy-2-(4-hydroxyphenyl)pyrrolo[2,1,5-cd]indolizine

A solution of 1-ethyl-6-methoxy-2-(4-methoxyphenyl)pyrrolo[2,1,5-cd]indolizine (115 mg, 0.337 mmol) in 3 ml of dichloromethane was cooled to –70° C. and 1.05 ml of a 1M boron tribromide solution in dichloromethane was added. When the addition was complete, the cooling source was removed and the mixture allowed to reach room temperature. The reaction mixture was poured into a stirred mixture of dichloromethane (125 ml) and a saturated sodium hydrogen carbonate solution (125 ml). The pH was adjusted to neutral with a 4M hydrochloric acid solution. The organic phase was separated and the aqueous phase further extracted with dichloromethane. The combined organic phases were dried and evaporated to leave 40 mg (40%) of the title compound as a semi solid substance. $^1$H-NMR (DMSO-$d_6$, 200 MHz) δ: 1.37 (t, 3H), 3.08 (q, 2H), 6.92–7.00 (m, 3H), 7.44–7.65 (m, 5H), 9.68 (s, 1H), 9.90 (s, 1H). (Compound 4).

EXAMPLE 5

6-Acetoxy-2-(4-acetoxyphenyl)-1-ethylpyrrolo[2,1,5-cd]indolizine

A mixture of 1-ethyl-6-hydroxy-2-(4-hydroxyphenyl)pyrrolo[2,1,5-cd]indolizine (32 mg, 0.12 mmol) and 0.043 ml of pyridine was stirred in a nitrogen atmosphere and 0.109 ml of acetic anhydride was added. Stirring was continued for half an hour and 15 ml of ice water was added. The mixture was extracted with dichloromethane and the combined extracts washed with dilute hydrochloride acid solution and finally with a saturated sodium hydrogen carbonate solution. The dried extract (magnesium sulfate) was evaporated to leave the title compound as a semi solid. $^1$H-NMR (DMSO-$d_6$, 200 MHz) d: $^1$H-NMR (DMSO-$d_6$, 200 MHz) δ: 1.40 (t, 3H), 2.36 (s, 3H), 2.43 (s, 3H), 3.22 (q, 2H), 7.33–7.40 (m, 3H), 7.82 (d, 1H), 7.88 (d, 2H), 7.96 (d, 1H), 8.08 (d, 1H). (Compound 5).

EXAMPLE 6

4-Acetyl-1-ethyl-6-methoxy-2-(4-methoxyphenyl)pyrrolo[2,1,5-cd]indolizine

A solution of 1-ethyl-7-methoxy-2-(4-methoxyphenyl)indolizine (Compound 3) (2.0 g, 7.11 mmol) in 65 ml of toluene was stirred in an ice bath, while 3-butyn-2-one (0.64 ml, 8.17 mmol) was added dropwise. The cooling source was removed and stirring was continued for twenty hours. 2,3-Dichloro-5,6-dicyano-1,4-benzoquinone (1.73 g, 7.61 mmol) was added in portions and stirring was continued for twenty hours. The solvent was evaporated and the residue chromatographed over aluminium oxide with heptane/tetrahydrofuran (1:1) as eluent to afford 1.54 g (63%) of the title compound. M.p. 137–39° C. $^1$H-NMR (DMSO-$d_6$, 200 MHz) δ: 1.39 (t, 3H), 2.64 (s, 3H), 3.15 (q, 2H), 3.87 (s, 3H), 4.09 (s, 3H), 7.19 (d, 2H), 7.80 (d, 2H), 7.82 (d, 1H), 7.89 (d, 1H), 8.15 (s, 1H). (Compound 6).

Analysis: Calculated for $C_{22}H_{21}N_1O_3$. C, 76.06; H, 6.09; N, 4.03%. Found: C, 76.07; H, 6.24; N, 3.68%.

EXAMPLE 7

4-Acetyl-1-ethyl-2-(4-hydroxyphenyl)-6-methoxypyrrolo[2,1,5-cd]indolizine

A solution of 4-acetyl-1-ethyl-6-methoxy-2-(4-methoxyphenyl)pyrrolo[2,1,5-cd]indolizine (0.3 g, 0.85 mmol) in 7 ml of dry dichloromethane was cooled to -65° C. and stirred in a nitrogen atmosphere while 1.2 ml of a 1 M boron tribromide solution in dichloromethane was added. Stirring was continued for one hour and the cooling source was removed. The reaction mixture was allowed to reach room temperature and then poured into a stirred medium of dichloromethane (100 ml) and a saturated sodium hydrogen carbonate solution (100 ml). The usual work up afforded 200 mg of a substance which was submitted to column chromatography (aluminium oxide) with dichloromethane/methanol (20:1) as eluent. The fractions having RF 0.4 (silica gel 60, dichloromethane/methanol (20:1)) was collected and evaporated to afford 160 mg (58%) of the title compound. M.p. 245–46° C. $^1$H-NMR (DMSO-$d_6$, 200 MHz) δ: 1.37 (t, 3H), 2.62 (s, 3H), 3.13 (q, 2H), 4.07 (s, 3H), 7.00 (d, 2H), 7.70 (d, 2H), 7.79 (d, 1H), 7.87 (d, 1H), 8.12 (s, 1H), 9.87 (s, 1H). (Compound 7).

EXAMPLE 8

4-Acetyl-1-ethyl-6-hydroxy-2-(4-hydroxyphenyl)pyrrolo[2,1,5-cd]indolizine

A solution of 4-acetyl-1-ethyl-6-methoxy-2-(4-methoxyphenyl)pyrrolo[2,1,5-cd]indolizine (0.2 g, 0.58 mmol) in 5 ml of dry dichloromethane was cooled to -65° C. and stirred in a nitrogen atmosphere, while 1.61 ml of a 1M boron tribromide solution in dichloromethane was added. The cooling source was removed and the mixture was stirred for seventy-two hours at room temperature. The mixture was neutralized with a saturated sodium hydrogen carbonate solution. The precipitate was isolated and dried to afford 177 mg (95%) of the title compound. M.p. 274–75° C. $^1$H-NMR (DMSO-$d_6$, 200 MHz) δ: 1.37 (t, 3H), 2.58 (s, 3H), 3.08 (q, 2H), 7.00 (d, 2H), 7.55 (d, 1H), 7.66 (d, 2H), 7.71 (d, 1H), 8.04 (s, 1H), 9.81 (s, 1H), 10.50 (s, 1H). (Compound 8).

Analysis: Calculated for $C_{20}H_{17}N_1O_3$, 1.25 $H_2O$. C, 70.26; H, 5.75; N, 4.10%. Found: C, 69.90; H, 5.31; N, 3.81%.

EXAMPLE 9

Methyl 6-methoxy-3-(4-methoxyphenyl)-4-methylpyrrolo[2,1,5-cd]indolizine-1-carboxylate A mixture of 7-methoxy-2-(4-methoxyphenyl)-1-methylindolizine (3.5 g, 13.1 mmol) (prepared in analogy with step 1–5 of example 1) in 120 ml of toluene was stirred in an ice bath, and methyl propiolate (1.45 ml, 16.2 mmol) was added dropwise. The cooling source was removed and the mixture was stirred and heated to 40° C. for six hours. 2,3-Dichloro-5,6-dicyano-1,4-benzoquinone (3.12 g, 13.7 mmol) was added in portions to the cooled mixture and stirring was continued for six hours at room temperature. The solvent was evaporated and the residue chromatograped over aluminium oxide with heptane/tetrahydrofuran (2:1) as eluent to afford 3.02 g (66%) of the title compound. M.p. 167–69° C. $^1$H-NMR (DMSO-$d_6$, 200 MHz) δ: 2.71 (s, 3H), 3.87 (s, 3H), 3.90 (s, 3H), 4.07 (s, 3H), 7.15 (d, 2H), 7.76 (d, 1H), 7.83 (d, 1H), 7.88 (d, 2H), 7.98 (s, 1H). (Compound 9).

The general synthetic principles outlined in example 1 have been applied to proper starting materials in the preparation of the following dimethyl dicarboxylate compounds:

EXAMPLE 10

Dimethyl 4-ethyl-3-(4-fluorophenyl)-6-methoxypyrrolo[2,1,5-cd]indolizine-1,2-dicarboxylate M.p. 141–43° C. $^1$H-NMR (DMSO-$d_6$, 200 MHz) δ: 1.35 (t, 3H), 3.08 (q, 2H), 3.71 (s, 3H), 3.88 (s, 3H), 4.08 (s, 3H), 7.35–7.65 (m, 4H), 7.85 (d, 1H), 8.04 (d, 1H). (Compound 10).

EXAMPLE 11

Dimethyl 6-methoxy-3-(4-methoxyphenyl)-4-methylpyrrolo[2,1,5-cd]indolizine-1,2-dicarboxylate M.p. 170–72° C. $^1$H-NMR (DMSO-$d_6$, 200 MHz) δ: 2.65 (s, 3H), 3.78 (s, 3H), 3.85 (s, 3H), 3.89 (s, 3H), 4.07 (s, 3H), 7.15 (d, 2H), 7.55 (d, 2H), 7.80 (d, 1H), 7.95 (d, 1H). (Compound 11).

EXAMPLE 12

Dimethyl 6-methoxy-4-methyl-3-phenylpyrrolo[2,1,5-cd]indolizine-1,2-dicarboxylate M.p. 172–74° C. $^1$H-NMR (DMSO-$d_6$, 200 MHz) δ: 2.66 (s, 3H), 3.75 (s, 3H), 3.90 (s, 3H), 4.08 (s, 3H), 7.45–7.65 (m, 5H), 7.84 (d, 1H), 7.98 (d, 1H). (Compound 12).

EXAMPLE 13

Dimethyl 4-ethyl-3-(4-methoxyphenyl)pyrrolo[2,1,5-cd]indolizine-1,2-dicarboxylate M.p. 136–38° C. $^1$H-NMR (DMSO-$d_6$, 200 MHz) δ: 1.39 (t, 3H), 3.12 (q, 2H), 3.79 (s, 3H), 3.87 (s, 3H), 3.93 (s, 3H), 7.17 (d, 2H), 7.54 (d, 2H), 8.08 (t, 1H), 8.34 (d, 1H), 8.40 (d, 1H). (Compound 13).

EXAMPLE 14

Dimethyl 4-ethyl-6-methoxy-3-phenylpyrrolo[2,1,5-cd]indolizine-1,2-dicarboxylate M.p. 151–52° C. $^1$H-NMR (DMSO-$d_6$, 200 MHz) δ: 1.37 (t, 3H), 3.08 (q, 2H), 3.71 (s, 3H), 3.90 (s, 3H), 4.10 (s, 3H), 7.45–7.60 (m, 5H), 7.87 (d, 1H), 8.03 (d, 3H). (Compound 14).

EXAMPLE 15

Dimethyl 3-(4-benzyloxyphenyl)pyrrolo[2,1,5-cd]indolizine-1,2-dicarboxylate

M.p. 157–59° C. $^1$H-NMR (DMSO-$d_6$, 200 MHz) δ: 3.95 (s, 6H), 5.20 (s, 2H), 7.25 (d, 2H), 7.35–7.55 (m, 5H), 7.77 (d, 2H), 7.82 (s, 1H), 8.11 (t, 1H), 8.24 (d, 1H), 8.41 (d, 1H). (Compound 15).

EXAMPLE 16

Dimethyl 7-benzyloxy-3-(4-benzyloxyphenyl)pyrrolo[2,1,5-cd]indolizine-1,2-dicarboxylate M.p. 159–60° C. $^1$H-NMR (DMSO-$d_6$, 200 MHz) δ: 3.75 (s, 3H), 3.85 (s, 3H), 5.18 (s, 2H), 5.50 (s, 2H), 7.12–7.78 (m, 16H), 8.15 (d, 1H). (Compound 16).

EXAMPLE 17

Dimethyl 6-methoxy-3-(4-methoxyphenyl)pyrrolo[2,1,5-cd]indolizine-1,2-dicarboxylate M.p. 135–36° C. $^1$H-NMR (DMSO-$d_6$, 200 MHz) δ: 3.86 (s, 3H), 3.92 (s, 3H), 3.95 (s, 3H), 4.09 (s, 3H), 7.14 (d, 2H), 7.62 (s, 1H), 7.74 (d, 2H), 7.83 (m, 2H). (Compound 17).

Analysis: Calculated for $C_{22}H_{19}N_1O_4$. C, 67.17; H, 4.87; N, 3.56%. Found: C, 67.08; H, 4.93; N, 3.39%.

EXAMPLE 18

Dimethyl 4-ethyl-3-(3-methoxyphenyl)pyrrolo[2,1,5-cd]indolizine-1,2-dicarboxylate $^1$H-NMR (DMSO-$d_6$, 200 MHz) δ: 1.40 (t, 3H), 3.16 (q, 2H), 3.76 (s, 3H), 3.82 (s, 3H), 3.85 (s, 3H), 7.05–7.56 (m, 4H), 8.08 (t, 1H), 8.38 (d, 1H), 8.42 (d, 1H). (Compound 18).

EXAMPLE 19

Dimethyl 4-ethyl-3-(3-fluoro-4-methoxyphenyl)pyrrolo[2,1,5-cd]indolizine-1,2-dicarboxylate M.p. 107–10° C. $^1$H-NMR (DMSO-$d_6$, 200 MHz) δ: 1.38 (t, 3H), 3.15 (q, 2H), 3.81 (s, 3H), 3.93 (s, 3H), 3.98 (s, 3H) 7.33–7.48 (m, 3H), 8.05 (t, 1H), 8.33 (d, 1H), 8.45 (d, 1H). (Compound 19).

EXAMPLE 20

Dimethyl 4-n-butyl-3-(4-methoxyphenyl)pyrrolo[2,1,5-cd]indolizine-1,2-dicarboxylate M.p. 102–3° C. $^1$H-NMR (DMSO-$d_6$, 200 MHz) δ: 0.87 (t, 3H), 1.37 (sext, 2H), 1.75 (quint, 2H), 3.12 (t, 2H), 3.78 (s, 3H), 3.86 (s, 3H), 3.93 (s, 3H), 7.16 (d, 2H), 7.52 (d, 2H), 8.08 (t, 1H), 8.32 (d, 1H), 8.42 (d, 1H). (Compound 20).

EXAMPLE 21

Dimethyl 4-ethyl-3-(4-methoxy-2-methylphenyl)pyrrolo[2,1,5-cd]indolizine-1,2-dicarboxylate M.p. 86–89° C. $^1$H-NMR (DMSO-$d_6$, 200 MHz) δ: 1.21 (t, 3H), 2.07 (s, 3H), 2.75 (m, 2H), 3.48 (s, 3H), 3.81 (s, 3H), 3.90 (s, 3H), 6.88 (dd, 1H), 6.98 (d, 1H), 7.20 (d, 1H), 8.03 (t, 1H), 8.32 (d, 1H), 8.41 (d, 1H). (Compound 21).

The above mentioned esters have been saponified in analogy with the method outlined in example 2 to afford the following dicarboxylic acid compounds:

EXAMPLE 22

4-Ethyl-3-(4-fluorophenyl)-6-methoxypyrrolo[2,1,5-cd]indolizine-1,2-dicarboxylic acid M.p. 217–18° C. $^{1}$H-NMR (DMSO-$d_6$, 200 MHz) δ: 1.32 (t, 3H), 3.02 (q, 2H), 4.08 (s, 3H), 7.30–7.65 (m, 4H), 7.92 (d, 2H), 7.98 (d, 2H). (Compound 22).

EXAMPLE 23

6-Methoxy-3-(4-methoxyphenyl)-4-methylpyrrolo[2,1,5-cd]indolizine-1,2-dicarboxylic acid M.p. 202–04° C. $^{1}$H-NMR (DMSO-$d_6$, 200 MHz) δ: 2.62 (s, 3H), 3.86 (s, 3H), 4.10 (s, 3H), 7.10 (d, 2H), 7.62 (d, 2H), 7.84 (d, 1H), 7.92 (d, 1H). (Compound 23).

EXAMPLE 24

4-Ethyl-3-(4-methoxyphenyl)pyrrolo[2,1,5-cd]indolizine-1,2-dicarboxylic acid

M.p. 228–29° C. $^{1}$H-NMR (DMSO-$d_6$, 200 MHz) δ: 1.38 (t, 3H), 3.02 (q, 2H), 3.86 (s, 3H), 7.12 (d, 2H), 7.60 (d, 2H), 8.04 (t, 1H), 8.31 (d, 1H), 8.42 (d, 1H). (Compound 24).

EXAMPLE 25

4-Ethyl-6-methoxy-3-phenylpyrrolo[2,1,5-cd]indolizine-1,2-dicarboxylic acid

M.p. 251–54° C. $^{1}$H-NMR (DMSO-$d_6$, 200 MHz) δ: 1.34 (t, 3H), 3.04 (q, 2H), 4.08 (s, 3H), 7.45–7.65 (m, 5H), 7.90 (d, 1H), 7.99 (d, 1H). (Compound 25).

EXAMPLE 26

3-(4-Benzyloxyphenyl)pyrrolo[2,1,5-cd]indolizine-1,2-dicarboxylic acid

M.p. 173–75° C. $^{1}$H-NMR (DMSO-$d_6$, 200 MHz) δ: 5.22 (s, 2H), 7.27 (d, 2H), 7.35–7.54 (m, 5H), 7.75 (s, 1H), 7.88 (d, 2H), 8.05 (t, 1H), 8,12 (d, 1H), 8.38 (d, 1H). (Compound 26).

EXAMPLE 27

7-Benzyloxy-3-(4-benzyloxyphenyl)pyrrolo[2,1,5-cd]indolizine-1,2-dicarboxylic acid $^{1}$H-NMR (DMSO-$d_6$, 200 MHz) δ: 5.20 (s, 2H), 5.52 (s, 2H), 7.10–7.83 (m, 16H), 8.12 (d, 1H). (Compound 27).

EXAMPLE 28

6-Methoxy-3-(4-methoxyphenyl)pyrrolo[2,1,5-cd]indolizine-1,2-dicarboxylic acid

M.p. 191–92° C. $^{1}$H-NMR (DMSO-$d_6$, 200 MHz) δ: 3.85 (s, 3H), 4.06 (s, 3H), 7.08 (d, 2H), 7.54 (s, 1H), 7.78–7.90 (m, 4H). (Compound 28).

EXAMPLE 29

4-Ethyl-3-(3-methoxyphenyl)pyrrolo[2,1,5-cd]indolizine-1,2-dicarboxylic acid

M.p. 217–20° C. $^{1}$H-NMR (DMSO-$d_6$, 200 MHz) δ: 1.39 (t, 3H), 3.14 (q, 2H), 6.99–7.50 (m, 4H), 8.05 (t, 1H), 8.35 (d, 1H), 8.45 (d, 1H). (Compound 29).

EXAMPLE 30

4-Ethyl-3-(3-fluoro-4-methoxyphenyl)pyrrolo[2,1,5-cd]indolizine-1,2-dicarboxylic acid M.p. 235–39° C. $^{1}$H-NMR (DMSO-$d_6$, 200 MHz) δ: 1.38 (t, 3H), 3.09 (q, 2H), 3.95 (s, 3H), 7.28–7.55 (m, 3H), 8.03 (t, 1H), 8.32 (d, 1H), 8.45 (d, 1H). (Compound 30).

EXAMPLE 31

4-n-Butyl-3-(4-methoxyphenyl)pyrrolo[2,1,5-cd]indolizine-1,2-dicarboxylic acid

M.p. 196–98° C. $^{1}$H-NMR (DMSO-$d_6$, 200 MHz) δ: 0.88 (t, 3H), 1.34 (sext, 2H), 1.72 (quint, 2H), 3.08 (t, 2H), 3.85 (s, 3H), 7.12 (d, 2H), 7.58 (d, 2H), 8.02 (t, 1H), 8.27 (d, 1H), 8.42 (d, 1H). (Compound 31).

EXAMPLE 32

4-Ethyl-3-(4-methoxy-2-methlyphenyl)pyrrolo[2,1,5-cd]indolizine-1,2-dicarboxylic acid M.p 216–18° C. $^{1}$H-NMR (DMSO-$d_6$, 200 MHz) δ: 1.18 (t, 3H), 2.05 (s, 3H), 2.80 (m, 2H), 3.83 (s, 3H), 6.82 (dd, 1H), 6.88 (d, 1H), 7.13 (d, 1H), 7.93 (t, 1H), 8.23 (d, 1H), 8.60 (d, 1H). (Compound 32).

The above mentioned dicarboxylic acids have been decarboxylated in analogy with the method outlined in example 3 to afford the following compounds:

EXAMPLE 33

1-Ethyl-2-(4-fluorophenyl)-6-methoxypyrrolo[2,1,5-cd]indolizine

M.p. 123–24° C. $^{1}$H-NMR (DMSO-$d_6$, 200 MHz) δ: 1.38 (t, 3H), 3.18 (q, 2H), 4.03 (s, 3H), 7.13 (d, 1H), 7.37–7.87 (m, 7H). (Compound 33).

Analysis: Calculated for $C_{19}H_{16}N_1F_1O_1$. C, 77.80; H, 5.50; N, 4.77%. Found: C, 78.02; H, 5.57; N, 4.57%.

EXAMPLE 34

1-Ethyl-2-(4-methoxyphenyl)pyrrolo[2,1,5-cd]indolizine $^{1}$H-NMR (DMSO-$d_6$, 200 MHz) δ: 1.42 (s, 3H), 3.24 (q, 2H), 3.86 (s, 3H), 7.18 (d, 2H), 7.32 (d, 1H), 7.71 (d, 1H), 7.74 (t, 1H), 7.78 (d, 2H), 8.08 (d, 1H), 8.13 (d, 1H). (Compound 34).

EXAMPLE 35

1-Ethyl-6-methoxy-2-phenylpyrrolo[2,1,5-cd]indolizine

M.p. 118–20° C. $^{1}$H-NMR (DMSO-$d_6$, 200 MHz) δ: 1.39 (t, 3H), 3.20 (q, 2H), 4.03 (s, 3H), 7.14 (d, 1H), 7.38–7.85 (m, 8H). (Compound 35).

EXAMPLE 36

1-Ethyl-2-(3-methoxyphenyl)pyrrolo[2,1,5-cd]indolizine $^{1}$H-NMR (DMSO-$d_6$, 200 MHz) δ: 1.43 (t, 3H), 3.27 (q, 2H), 3.88 (s, 3H), 7.00–7.81 (m, 7H), 8.12 (d, 1H), 8.21 (d, 1H). (Compound 36).

Analysis: Calculated for $C_{19}H_{17}N_1O_1$. C, 82.88; H, 6.22; N, 5.09%. Found: C, 82.86; H, 6.31; N, 4.85%.

EXAMPLE 37

5-Benzyloxy-2-(4-benzyloxyphenyl)pyrrolo[2,1,5-cd]indolizine

M.p. 155–56° C. $^{1}$H-NMR (DMSO-$d_6$, 200 MHz) δ: 5.19 (s, 2H), 5.49 (s, 2H), 7.15 (d, 2H), 7.35–7.93 (m, 15H), 8.05 (d, 2H). (Compound 37).

EXAMPLE 38

6-Methoxy-2-(4-methoxyphenyl)pyrrolo[2,1,5-cd]indolizine

M.p. 147–48° C. $^1$H-NMR (DMSO-d$_6$, 200 MHz) δ: 3.85 (s, 3H), 4.00 (s, 3H), 7.10 (d, 2H), 7.22 (d, 1H), 7.46 (s, 1H), 7.69 (m, 2H), 7.95 (d, 1H), 8.08 (d, 2H). (Compound 38).

Analysis: Calculated for C$_{18}$H$_{15}$N$_1$O$_2$. C, 77.96; H, 5.45; N, 5.05%. Found: C, 78.18; H, 5.51; N, 4.94%.

EXAMPLE 39

2-(4-Benzyloxyphenyl)pyrrolo[2,1,5-cd]indolizine

M.p. 161–62° C. $^1$H-NMR (DMSO-d$_6$, 200 MHz) δ: 5.22 (s, 2H), 7.19 (d, 2H), 7.35–7.55 (m, 6H), 7.68–7.82 (m, 2H), 8.00–8.15 (m, 5H). (Compound 39).

EXAMPLE 40

1-Ethyl-2-(3-fluoro-4-methoxyphenyl)pyrrolo[2,1,5-cd]indolizine

M.p. 77–79° C. $^1$H-NMR (DMSO-d$_6$, 200 MHz) δ: 1.41 (t, 3H), 3.25 (q, 2H), 3.95 (s, 3H), 7.30–7.43 (m, 2H), 7.55–7.70 (m, 4H), 8.12 (d, 1H), 8.18 (d, 1H). (Compound 40).

EXAMPLE 41

1-n-Butyl-2-(4-methoxyphenyl)pyrrolo[2,1,5-cd]indolizine

M.p. 48–50° C. $^1$H-NMR (DMSO-d$_6$, 200 MHz) δ: 0.92 (t, 3H), 1.41 (sext, 2H), 1.78 (quint, 2H), 3.20 (q, 2H), 3.85 (s, 3H), 7.15 (d, 2H), 7.31 (d, 1H), 7.69 (d, 1H), 7.73 (t, 1H), 7.78 (d, 2H), 8.07 (d, 1H), 8.12 (d, 1H). (Compound 41).

EXAMPLE 42

1-Ethyl-2-(4-methoxy-2-methylphenyl)pyrrolo[2,1,5-cd]indolizine

M.p. 56–59° C. $^1$H-NMR (DMSO-d$_6$, 200 MHz) δ: 1.28 (t, 3H), 2.21 (s, 3H), 2.95 (q, 2H), 3.83 (s, 3H), 6.93 (dd, 1H), 7.02 (d, 1H), 7.28 (d, 1H), 7.32 (d, 1H), 7.49 (d, 1H), 7.75 (t, 3H), 8.00 (d, 1H), 8.05 (d, 1H). (Compound 42).

EXAMPLE 43

4-Acetyl-1-ethyl-2-(4-methoxyphenyl)pyrrolo[2,1,5-cd]indolizine

The title compound was prepared in analogy with the method outlined in example 6. M.p. 73–75° C. $^1$H-NMR (DMSO-d$_6$, 200 MHz) δ: 1.41 (t, 3H), 2.68 (s, 3H), 3.21 (q, 2H), 3.88 (s, 3H), 7.17 (d, 2H), 7.81 (d, 2H), 7.97 (t, 1H), 8.19 (d, 1H), 8.26 (s, 1H), 8.39 (d, 1H). (Compound 43).

The above mentioned methoxy derivatives have been partly or fully deprotected in analogy with the methods outlined in examples 7 or 8 to afford the following compounds:

EXAMPLE 44

6-Hydroxy-2-(4-methoxyphenyl)pyrrolo[2,1,5-cd]indolizine $^1$H-NMR (DMSO-d$_6$, 200 MHz) δ: 3.98 (s, 3H), 6.92 (d, 2H), 7.18 (d, 1H), 7.41 (s, 1H), 7.62–7.69 (m, 2H), 7.88–7.98 (m, 3H). (Compound 44).

EXAMPLE 45

6-Hydroxy-2-(4-hydroxyphenyl)pyrrolo[2,1,5-cd]indolizine $^1$H-NMR (DMSO-d$_6$, 200 MHz) δ: 6.92 (d, 2H), 7.08 (d, 1H), 7.32 (s, 1H), 7.40–7.44 (m, 2H), 7.85 (d, 1H), 7.92 (d, 2H). (Compound 45).

EXAMPLE 46

1-Ethyl-6-hydroxy-2-phenylpyrrolo[2,1,5-cd]indolizine $^1$H-NMR (DMSO-d$_6$, 200 MHz) δ: 1.38 (t, 3H), 3.25 (q, 2H), 7.05 (d, 1H), 7.40–7.62 (m, 6H), 7.80 (d, 2H). (Compound 46).

EXAMPLE 47

1-Ethyl-2-(3-hydroxyphenyl)pyrrolo[2,1,5-cd]indolizine

M.p. 56–58° C. $^1$H-NMR (DMSO-d$_6$, 200 MHz) δ: 1.42 (t, 3H), 3.25 (q, 2H), 6.82–6.90 (m, 1H), 7.24–7.44 (m, 4H), 7.68–7.82 (m, 2H), 8.10–8.22 (m, 2H), 9.68 (s, 1H). (Compound 47).

EXAMPLE 48

4-Acetyl-1-ethyl-2-(4-hydroxyphenyl)pyrrolo[2,1,5-cd]indolizine

M.p. 183–84° C. $^1$H-NMR (DMSO-d$_6$, 200 MHz) δ: 1.41 (t, 3H), 3.21 (q, 2H), 7.00 (d, 2H), 7.71 (d, 2H), 7.96 (t, 1H), 8.18 (d, 1H), 8.27 (s, 1H), 8.39 (d, 1H). (Compound 48).

Analysis: Calculated for C$_{20}$H$_{17}$N$_1$O$_2$. C, 79.19; H, 5.65; N, 4.62%. Found: C, 79.09; H, 5.68; N, 4.33%.

EXAMPLE 49

1-Ethyl-2-(3-fluoro-4-hydroxyphenyl)pyrrolo[2,1,5-cd]indolizine $^1$H-NMR (DMSO-d$_6$, 200 MHz) δ: 1.38 (t, 3H), 3.23 (q, 2H), 7.20 (f, 1H), 7.33 (d, 1H), 7.45–7.78 (m, 4H), 8.03 (d, 1H), 8.08 (d, 1H), 10.21 (s, 1H). (Compound 49).

EXAMPLE 50

1-Ethyl-2-(4-hydroxy-2-methylphenyl)pyrrolo[2,1,5-cd]indolizine $^1$H-NMR (DMSO-d$_6$, 200 MHz) δ: 1.22 (t, 3H), 2.13 (s, 1H), 2.93 (q, 2H), 6.70 (dd, 1H), 6.78 (d, 1H), 7.18 (d, 1H), 7.22 (d, 1H), 7.45 (d, 1H), 7.68 (t, 1H), 8.03 (d, 1H), 8.08 (d, 1H). (Compound 50).

EXAMPLE 51

1-n-Butyl-2-(4-hydroxyphenyl)pyrrolo[2,1,5-cd]indolizine $^1$H-NMR (DMSO-d$_6$, 200 MHz) δ: 0.92 (t, 3H), 1.40 (sext, 2H), 1.67 (quint, 2H), 3.18 (q, 2H), 6.97 (d, 2H), 7.29 (d, 1H), 7.15 (d, 2H), 7.18 (d, 1H), 7.21 (t, 1H), 8.04 (d, 1H), 8.09 (d, 1H). (Compound 51).

EXAMPLE 52

1-Ethyl-2-(4-hydroxyphenyl)pyrrolo[2,1,5-cd]indolizine

A solution of 1-ethyl-2-(4-methoxyphenyl)pyrrolo[2,1,5-cd]indolizine (Compound 34) (0.77 g, 2.79 mmol) in 25 ml of dry dichloromethane was stirred under a nitrogen atmosphere and aluminium chloride (2.23 g, 16.7 mmol) was added in portions. When the addition was complete, ethanethiol (1.25 ml, 16.7 mmol) was added, and stirring was continued for half an hour. The mixture was cooled in an ice bath followed by the addition of tetrahydrofuran (15 ml), 6M hydrochloric acid (3 ml), water (50 ml) and ethyl acetate (100 ml). The organic phase was separated and evaporated to leave a residue which was chromatograped over silica gel with toluene/ethyl acetate (4:1) as eluent. The proper fractions were collected and evaporated, and the residue was triturated with a mixture of ether (2 ml) and petroleum ether (5 ml) to afford 0.32 g (44%) of the title compound. M.p. 104–05° C. $^1$H-NMR (DMSO-$d_6$, 200 MHz) δ: 1.41 (t, 3H), 3.22 (q, 2H), 6.98 (d, 2H), 7.29 (d, 1H), 7.67 (d, 2H), 7.69(d, 1H), 7.72(t, 1H), 8.05 (d, 1H), 8.10 (d, 1H), 9.68 (s, 1H). (Compound 52).

Analysis: Calculated for $C_{18}H_{15}N_1O_1$. C, 82.73; H, 5.79; N, 5.36%. Found: C, 83.03; H, 5.88; N, 5.16%.

EXAMPLE 53

5-Hydroxy-2-(4-hydroxyphenyl)pyrrolo[2,1,5-cd] indolizine

A solution of 5-benzyloxy-2-(4-benzyloxyphenyl)pyrrolo [2,1,5-cd]indolizine (48 mg, 0.11 mmol) in 2 ml of tetrahydrofuran and 3 ml of ethanol was hydrogenated in the presence of 10% palladium on carbon (30 mg). When the theoretical amount of hydrogen had been consumed the catalyst was filtered off and the filtrate was evaporated to afford 27 mg (99%) of the title compound. M.p. 165° C. (dec.). $^1$H-NMR (DMSO-$d_6$, 200 MHz) δ: 6.92 (d, 2H), 7.15 (d, 1H), 7.36 (d, 1H), 7.43 (s, 1H), 7.73 (d, 1H), 7.88 (d, 2H). (Compound 53).

Analysis: Calculated for $C_{16}H_{11}N_1O_2$, 0.5 $H_2O$. C, 74.41; H, 4.68; N, 5.42%. Found: C, 74.66; H, 4.45; N, 5.03%.

EXAMPLE 54

2-(4-Hydroxyphenyl)pyrrolo[2,1,5-cd]indolizine

The title compound was prepared in analogy with the method outlined in example 52. M.p. 194–95° C. (dec.). 1H-NMR (DMSO-$d_6$, 200 MHz) δ: 6.94 (d, 2H), 7.48 (d, 1H), 7.59 (s, 1H), 7.73 (t, 1H), 7.95–8.08 (m, 5H), 9.78 (s, 1H). (Compound 54).

What is claimed is:

1. A compound of formula I

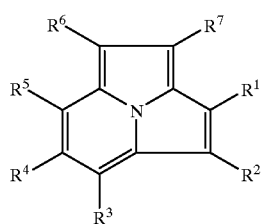

(I)

wherein $R^1$ is phenyl substituted with one or two substituents selected from halogen, OH, $OCH_3$, $OCOCH_3$ or benzyloxy; and $R^2$ is H, $C_{1-4}$-alkyl or CO—$R^8$—O—$R^9$—$NR^{10}R^{11}$, wherein $R^8$ is phenylene, $R^9$ is $C_{1-2}$-alkylene and $R^{10}$ and $R^{11}$ together with the nitrogen atom form a piperidino ring; and $R^3$ is H; and $R^4$ is H, OH, $OCH_3$ or $OCOCH_3$; and $R^5$ is H, OH or benzyloxy; and $R^6$ is H, halogen, $C_{1-2}$-alkyl, $COCH_3$, COOH, $COOCH_3$, CO—$R^{12}$—$NR^{13}R^{14}$, $R^{15}$—$NR^{13}R^{14}$ or phenyl optionally substituted with OH or benzyloxy, wherein $R^{12}$ is $C_{1-2}$-alkylene, $R^{15}$ is $C_{1-7}$-alkylene and $R^{13}$ and $R^{14}$ together with the nitrogen atom form a piperidino ring; and $R^7$ is H, halogen, $C_{1-2}$-alkyl, $COCH_3$, COOH, $COOCH_3$, CO—$NR^{16}R^{17}$, O—$R^{18}$—O—$R^{19}$—$NR^{20}R^{21}$, CO—$R^{18}$—O—$R^{19}$—$NR^{20}R^{21}$, $R^{18}$—O—$R^{19}$—$NR^{20}R^{21}$ or $R^{22}$—$NR^{20}R^{21}$, wherein $R^{16}$ and $R^{17}$ independently are H or $CH_3$, $R^{18}$ is phenylene, $R^{19}$ is $C_{1-2}$-alkylene, $R^{20}$ and $R^{21}$ together with the nitrogen atom form a piperidino ring and $R^{22}$ is $C_{1-7}$-alkylene, or geometric or optical isomers, pharmaceutically acceptable esters, ethers or salts thereof.

2. A compound according to claim 1 in which $R^1$ is phenyl optionally substituted with OH or $OCH_3$.

3. A compound according to claim 1 in which $R^2$ is $C_{1-3}$-alkyl.

4. A compound according to claim 1 in which $R^4$ is H, OH or $OCH_3$.

5. A compound according to claim 1 in which $R^5$ is H or OH.

6. A compound according to claim 1 in which $R^6$ is CO—$R^{12}$—$NR^{13}R^{14}$ or $R^{15}$—$NR^{13}R^{14}$ and $R^{15}$ is $C_{4-7}$-alkylene.

7. A compound according to claim 1 in which $R^7$ is $R^{18}$—O—$R^{19}$—$NR^{20}R^{21}$ or $R^{22}$—$NR^{20}R^{21}$ and $R^{22}$ is $C_{4-7}$-alkylene.

8. A compound according to claim 1 in which $R^1$ is phenyl optionally substituted with OH.

9. A compound according to claim 1 in which $R^2$ is $C_{1-3}$-alkyl.

10. A compound according to claim 1 in which $R^4$ is $OCH_3$.

11. A compound according to claim 1 in which $R^5$ is H.

12. A compound according to claim 1 in which $R^6$ is CO—$R^{12}$—$N^{13}R^{14}$.

13. A compound according to claim 1 in which $R^7$ is $R^{18}$—O—$R^{19}$—$NR^{20}R^{21}$.

14. A compound selected from the following:

Dimethyl 4-ethyl-6-methoxy-3-(4-methoxyphenyl)pyrrolo [2,1,5-cd]indolizine-1,2-dicarboxylate, 4-Ethyl-6-methoxy-3-(4-methoxyphenyl)pyrrolo[2,1,5-cd] indolizine-1,2-dicarboxylic acid, 1-Ethyl-6-methoxy-2-(4-methoxyphenyl)pyrrolo[2,1,5-cd] indolizine, 1-Ethyl-6-hydroxy-2-(4-hydroxyphenyl)pyrrolo[2,1,5-cd] indolizine, 6-Acetoxy-2-(4acetoxyphenyl)-1-ethylpyrrolo[2,1,5-cd] indolizine, 4-Acetyl-1-ethyl-6-methoxy-2-(4-methoxyphenyl)pyrrolo [2,1,5-cd]indolizine, 4-Acetyl-1-ethyl-2-(4-hydroxyphenyl)-6-methoxypyrrolo [2,1,5-cd]indolizine, 4-Acetyl-1-ethyl-6-hydroxy-2-(4-hydroxyphenyl)pyrrolo[2, 1,5-cd]indolizine, Methyl 6-methoxy-3-(4-methoxyphenyl)-4-methylpyrrolo [2,1,5-cd]indolizine-1-carboxylate, Dimethyl 4-ethyl-3-(4-fluorophenyl)-6-methoxypyrrolo[2, 1,5-cd]indolizine-1,2-dicarboxylate, Dimethyl 6-methoxy-3-(4-methoxyphenyl)-4-methylpyrrolo[2,1,5-cd]indolizine-1,2-dicarboxylate, Dimethyl 4-ethyl-3-(4-methoxyphenyl)pyrrolo[2,1,5-cd] indolizine-1,2-dicarboxylate, Dimethyl 3-(4-benzyloxyphenyl)pyrrolo[2,1,5-cd] indolizine-1,2-dicarboxylate, Dimethyl 7-benzyloxy-3-(4-benzyloxyphenyl)pyrrolo[2,1,5-cd]indolizine-1,2-dicarboxylate,
Dimethyl 6-methoxy-3-(4-methoxyphenyl)pyrrolo[2,1,5-cd]indolizine-1,2-dicarboxylate,
Dimethyl 4-ethyl-3-(3-methoxyphenyl)pyrrolo[2,1,5-cd]indolizine-1,2-dicarboxylate,
Dimethyl 4-ethyl-3-(3-fluoro-4-methoxyphenyl)pyrrolo[2,1,5-cd]indolizine-1,2-dicarboxylate,
Dimethyl 4-n-butyl-3-(4-methoxyphenyl)pyrrolo[2,1,5-cd]indolizine-1,2-dicarboxylate,
4-Ethyl-3-(4-fluorophenyl)-6-methoxypyrrolo[2,1,5-cd]indolizine-1,2-dicarboxylic acid,
6-Methoxy-3-(4-methoxyphenyl)-4-methylpyrrolo[2,1,5-cd]indolizine-1,2-dicarboxylic acid,
4-Ethyl-2-(4-methoxyphenyl)pyrrolo[2,1,5-cd]indolizine1,2-dicarboxylic acid,
3-(4-Benzyloxyphenyl)pyrrolo[2,1,5-cd]indolizine-1,2-dicarboxylic acid,
7-Benzyloxy-3-(4-benzyloxyphenyl)pyrrolo[2,1,5-cd]indolizine-1,2-dicarboxylic acid,
6-Methoxy-3-(4-methoxyphenyl)pyrrolo[2,1,5-cd]indolizine-1,2-dicarboxylic acid,
4-Ethyl-3-(3-methoxyphenyl)pyrrolo[2,1,5-cd]indolizine-1,2-dicarboxylic acid,
4-Ethyl-3-(3-fluoro-4-methoxyphenyl)pyrrolo[2,1,5-cd]indolizine-1,2-dicarboxylic acid,
4-n-Butyl-3-(4-methoxyphenyl)pyrrolo[2,1,5-cd]indolizine-1,2-dicarboxylic acid,
1-Ethyl-2-(4-fluorophenyl)-6-methoxypyrrolo[2,1,5-cd]indolizine,
1-Ethyl-2-(4-methoxyphenyl)pyrrolo[2,1,5-cd]indolizine,
1-Ethyl-2-(3-methoxyphenyl)pyrrolo[2,1,5-cd]indolizine,
5-Benzyloxy-2-(4-benzyloxyphenyl)pyrrolo[2,1,5-cd]indolizine,
6-Methoxy-2-(4-methoxyphenyl)pyrrolo[2,1,5-cd]indolizine,
2-(4-Benzyloxyphenyl)pyrrolo[2,1,5-cd]indolizine,
1-Ethyl-2-(3-fluoro-4-methoxyphenyl)pyrrolo[2,1,5-cd]indolizine,
1-n-Butyl-(4-(methoxyphenyl)pyrrolo[2,1,5-cd]indolizine
4-Acetyl-1-ethyl-2-(4-methoxyphenyl)pyrrolo[2,1,5-cd]indolizine,
6-Hydroxy-2-(4-methoxyphenyl)pyrrolo[2,1,5-cd]indolizine,
6-Hydroxy-2-(4-hydroxyphenyl)pyrrolo[2,1,5-cd]indolizine,
1-Ethyl-2-(3-hydroxyphenyl)pyrrolo[2,1,5-cd]indolizine,
4Acetyl-1-ethyl-2-(4-hydroxyphenyl)pyrrolo[2,1,5-cd]indolizine,
1-Ethyl-2-(3-fluoro-4-hydroxyphenyl)pyrrolo[2,1,5-cd]indolizine,
1-Ethyl-2-(4-hydroxy-2-methylphenyl)pyrrolo[2,1,5-cd]indolizine,
1-n-Butyl-2-(4hydroxyphenyl)pyrrolo[2,1,5-cd]indolizine,
1-Ethyl-2-(4-hydroxyphenyl)pyrrolo[2,1,5-cd]indolizine,
5-Hydroxy-2-(4-hydroxyphenyl)pyrrolo[2,1,5-cd]indolizine,
2-(4-Hydroxyphenyl)pyrrolo[2,1,5-cd]indolizine,
1-Ethyl-6-hydroxy-2-(4-hydroxyphenyl)-3-[4-(2-piperidinoethoxy)benzoyl]pyrrolo[2,1,5-cd]indolizine,
1-Ethyl-2-(4-hydroxyphenyl)-3-(6-piperidinohexyl)pyrrolo[2,1,5-cd]indolizine,
1-Ethyl-2-(4-hydroxyphenyl)-3-[4-(2-piperidinoethoxy)benzoyl]pyrrolo[2,1,5-cd]indolizine,
1-Ethyl-2-(3-fluoro-4-hydroxyphenyl)-3-[4-(2-piperidinoethoxy)phenyl]pyrrolo[2,1,5-cd]indolizine,
1-Ethyl-2-(4-hydroxyphenyl)-4-(1-oxo-3-piperidinopropyl)pyrrolo[2,1,5-cd]indolizine,
1,4-Diethyl-2-(4-hydroxyphenyl)pyrrolo[2,1,5-cd]indolizine,
1-Ethyl-2-(4-methoxyphenyl)-4-(3-piperidinopropyl)pyrrolo[2,1,5-cd]indolizine,
1-ethyl-2-(4-hydroxyphenyl)-4-(3-piperidinopropyl)pyrrolo[2,1,5-cd]indolizine,
1-Ethyl-2-(4-methoxyphenyl)-4-phenylpyrrolo[2,1,5-cd]indolizine,
1-Ethyl-2-(4-hydroxphenyl)-4-phenylpyrrolo[2,1,5-cd]indolizine,
1-Ethyl-4-(4-hydroxyphenyl)-2-(4-methoxyphenyl)pyrrolo[2,1,5-cd]indolizine,
1-Ethyl-2,4-bis-(4-hydroxyphenyl)pyrrolo[2,1,5-cd]indolizine,
1-Ethyl-2-(4-hydroxyphenyl)-3-methylpyrrolo[2,1,5-cd]indolizine,
4-Ethyl-3-(4-hydroxyphenyl)pyrrolo[2,1,5-cd]indolizine-2-carboxylic acid dimethylamide,
2-(4-Methoxyphenyl)-3-(4-(2-piperidinoethoxy)phenyl)pyrrolo[2,1,5-cd]indolizine,
2-(4-Hydroxyphenyl)-3-(4-(2-piperidinoethoxy)phenyl)pyrrolo[2,1,5-cd]indolizine,
1-Ethyl-2-(4-hydroxyphenyl)-3-(4-(2-piperidinoethoxy)phenyl)pyrrolo[2,1,5-cd]indolizine,
1-Ethyl-2-(4-methoxyphenyl)-3-(4-(2-piperidinoethoxy)phenyl)pyrrolo[2,1,5-cd]indolizine;

or geometric or optical isomers, pharmaceutically acceptable esters, ethers or salts thereof.

15. A pharmaceutical composition comprising an estrogen agonistic effective amount of a compound of claim 1, together with a pharmaceutically acceptable carrier or diluent.

16. A pharmaceutical composition according to claim 15 in the form of an oral dosage unit or parenteral dosage unit.

17. A method for treating estrogen deficiency, comprising administering to a mammal in need thereof an estrogen agonistic effective amount of a compound of claim 1.

* * * * *

UNITED STATES PATENT AND TRADEMARK OFFICE
CERTIFICATE OF CORRECTION

PATENT NO. : 6,075,036
DATED : June 13, 2000
INVENTOR(S) : Jorgensen et al.

It is certified that error appears in the above-identified patent and that said Letters Patent is hereby corrected as shown below:

Column 26,
Line 47, claim 16 delete "A" and insert --The--.

Signed and Sealed this

Seventeenth Day of July, 2001

*Attest:*

Nicholas P. Godici

*Attesting Officer*

NICHOLAS P. GODICI
*Acting Director of the United States Patent and Trademark Office*